United States Patent
Goebel et al.

(10) Patent No.: US 6,350,260 B1
(45) Date of Patent: Feb. 26, 2002

(54) CATHETER COUPLING

(75) Inventors: Udo Goebel, Melsungen-Kirchhof; Hans-Joachim Otto; Martin Sippel, both of Melsungen, all of (DE)

(73) Assignee: B. Braun Melsungen AG, Melsungen (DE)

(*) Notice: Subject to any disclaimer, the term of this patent is extended or adjusted under 35 U.S.C. 154(b) by 0 days.

(21) Appl. No.: 09/512,027

(22) Filed: Feb. 24, 2000

(30) Foreign Application Priority Data

Feb. 24, 1999 (DE) .................................... 299 03 286 U

(51) Int. Cl.[7] .............................................. A61M 25/16
(52) U.S. Cl. ....................................... 604/533; 604/537
(58) Field of Search ........................ 604/523, 533–539, 604/905; 606/157–158; D28/39–43

(56) References Cited

U.S. PATENT DOCUMENTS

| D99,563 | S | * | 5/1936 | Schmitt |
| D149,025 | S | * | 3/1948 | Sawyer |
| 2,464,739 | A | * | 3/1949 | Solomon et al. |
| 4,006,744 | A | | 2/1977 | Steer |
| 4,429,852 | A | * | 2/1984 | Tersteegen et al. ............ 251/9 |
| 4,453,295 | A | * | 6/1984 | Laszczower ................. 251/10 |
| RE32,338 | E | * | 1/1987 | Alexander et al. ............ 294/16 |
| 5,368,573 | A | * | 11/1994 | Andrew ...................... 604/158 |
| 5,423,776 | A | | 6/1995 | Haindl |
| 5,465,742 | A | * | 11/1995 | Dudley ....................... 132/279 |
| 5,501,693 | A | * | 3/1996 | Gravener .................... 606/157 |
| 5,531,695 | A | * | 7/1996 | Swisher ...................... 604/111 |
| 5,921,996 | A | * | 7/1999 | Sherman .................... 606/157 |
| D429,030 | S | * | 8/2000 | Yasuda ........................ D28/40 |

FOREIGN PATENT DOCUMENTS

EP 0415665 8/1990

* cited by examiner

Primary Examiner—Sharon Kennedy
(74) Attorney, Agent, or Firm—Diller, Ramik & Wight

(57) ABSTRACT

The catheter coupling is intended for providing the proximal end of a catheter with a plug connector forming a fluid transfer connection. The catheter coupling comprises two pivotable jaws enclosing a wavy channel. One of the jaws is provided with a hose in which the catheter may be inserted. When the other jaw is closed, the hose and the catheter is deformed to a wave-shape without any significant change in cross section. Thus, the catheter is secured against being pulled out.

20 Claims, 5 Drawing Sheets

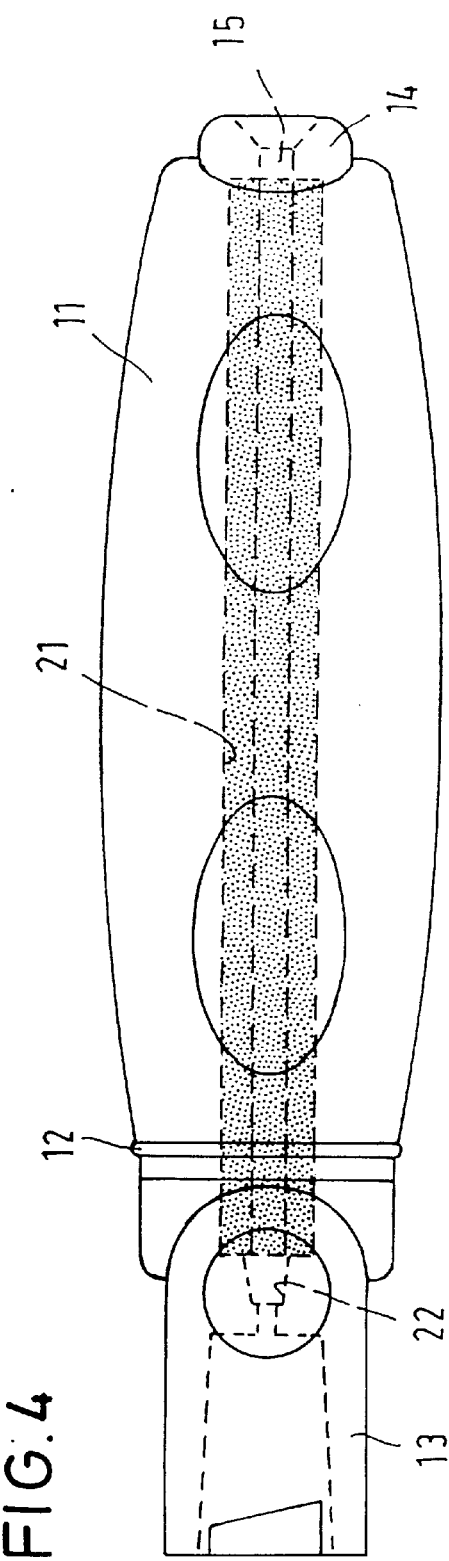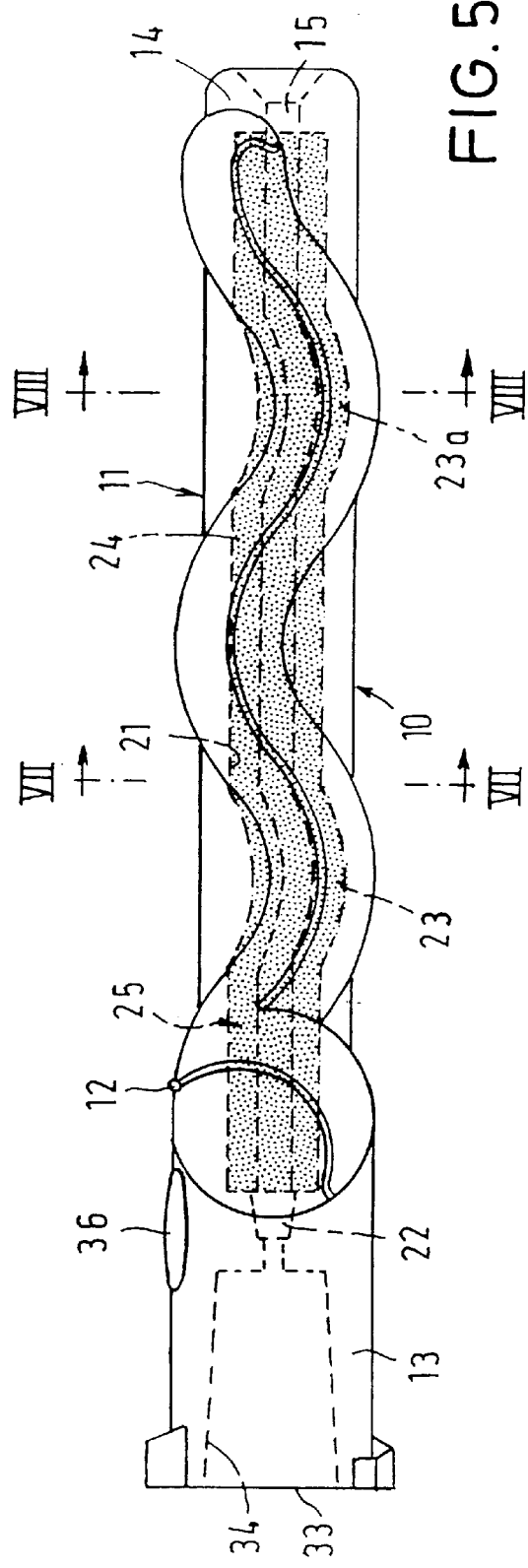

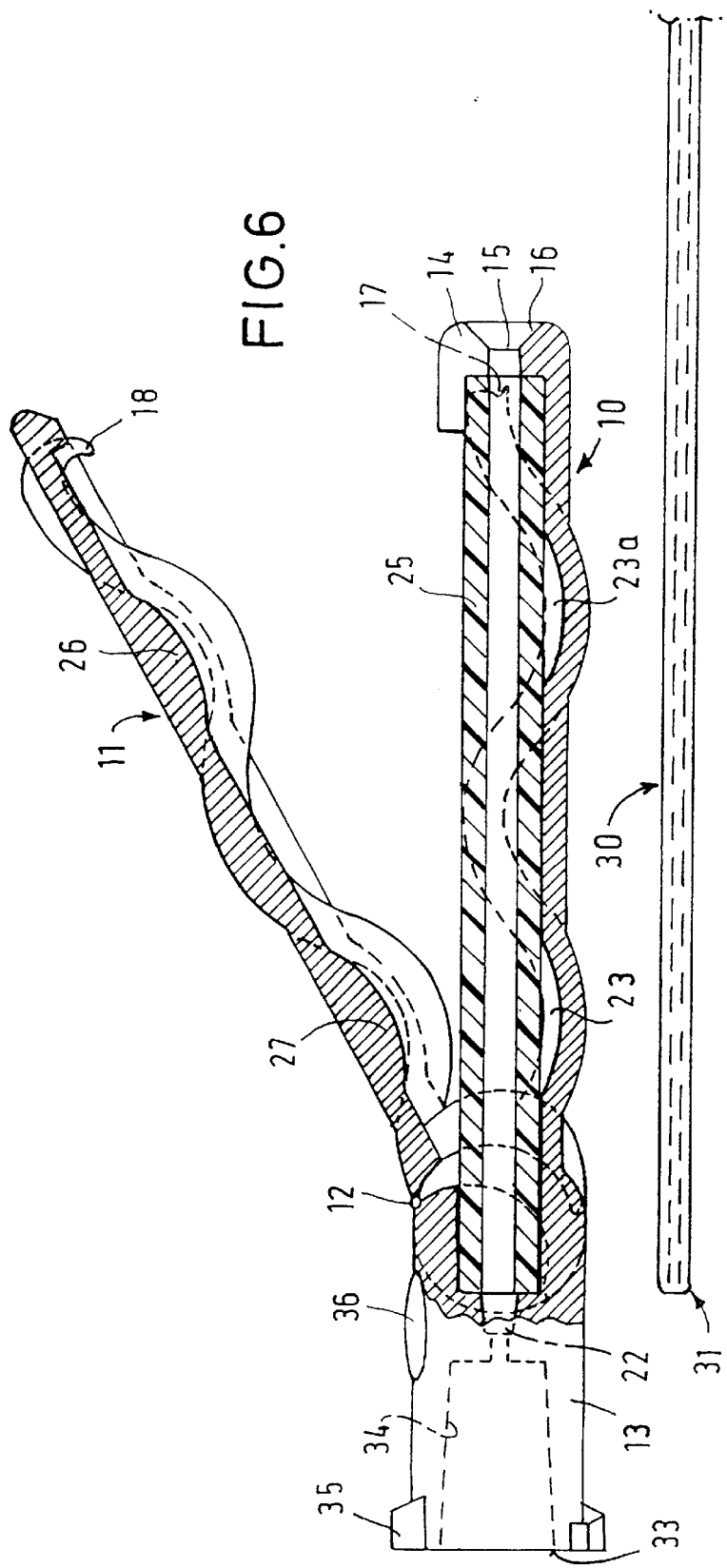
FIG. 6
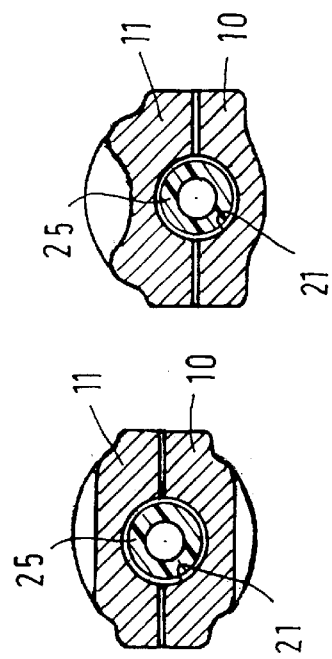
FIG. 7
FIG. 8

CATHETER COUPLING

BACKGROUND OF THE INVENTION

The present invention refers to a catheter coupling with integrated strain relief for allowing a catheter to be coupled to a syringe or to another liquid transfer device.

In epidural anesthesia, a catheter is introduced into the epidural space of a patient through a steel cannula. Subsequently, the steel cannula is withdrawn beyond the proximal catheter end, whereas the catheter remains in its position. The proximal end of the catheter must not have any enlargements or connecting devices, since the withdrawal of the steel cannula would be hindered thereby. After removal of the steel cannula, the catheter must be provided with a catheter coupling, e.g. in the form of a Luer-Lock connector, for connection to liquid supplying device. The catheter consists of a flexible hose with a small diameter. The outer diameter is generally less than 1 mm. A catheter coupling connected to the catheter must not squeeze the catheter so that the catheter lumen stays open.

From EP 0 415 665 A1, a catheter coupling is known, wherein the catheter is passed through an annular elastomer plug clamped between two screwed elements. By tightening the screw elements, the plug is rotated radially and pressed against the catheter with force. To operate the catheter coupling, two hands are required, while having to hold the catheter at the same time. An appropriate tightening of the catheter coupling would thus require three hands. Moreover, the tightening requires great strength. When the catheter coupling has a Luer-Lock connector having to be turned for disengagement, there is a risk that the catheter coupling is opened instead of the Luer-Lock connector so that the catheter slips out.

Another hose coupling is described in U.S. Pat. No. 5 423 766. Here, the catheter coupling includes a trumpet-shaped tube member, the catheter being slipped onto the narrower end thereof. Subsequently, the clamping is performed with two clamping members tensioned by means of a bayonet catch. Again, inadvertently turning the bayonet catch may cause disengagement.

A catheter coupling with two articulated jaws is known from U.S. Pat. No. 4 006 744. Here, one of the jaws is provided with a hose piece through which the catheter is passed. The other jaw is folded over the hose piece, clamping the same. The catheter is held only by the radially pressed hose piece. In this case, there is a risk of inadvertently pulling out the catheter.

SUMMARY OF THE INVENTION

It is an object of the present invention to provide a catheter coupling with strain relief that is simple to apply to the catheter and guarantees a great holding force, without constricting the catheter.

According to the present invention, the jaws extend in the longitudinal direction of the hose piece receiving the catheter end and they are connected at the one end of the hose piece by a joint whose axis extends transversely to the hose piece. At the opposite end the jaws may be locked in the closed state. Thus, the end portion of the catheter to be clamped is engaged by the jaws in the longitudinal direction, thereby guaranteeing a-particularly good and safe hold, since a long covered portion can be realized. Further, when closing the jaws, the clamping force progressively increases from one end to the other. In this manner, a safe clamping is achieved over a relatively long distance.

Preferably, the grooves in the jaws that form the channel, does not have a continuous groove bottom, but the groove bottom has rises and indentations, to cause a wavy path of the hose piece when the jaws are closed. This generates high frictional resistance.

The catheter coupling is very easy to handle. It is only necessary to press the jaws against each other to close the channel. Moreover, there is no risk of the catheter coupling being inadvertently opened by turning movements as they are necessary for disengagement from a counter plug connector.

Preferably, the channel has at least two bends with a straight section in between. Here, the hose is deformed only in the bends, but not in the straight portion. This way, it is made sure that, with the jaws open, the hose assumes a stretched straight state so that the catheter can easily be introduced into the hose.

BRIEF DESCRIPTION OF THE DRAWINGS

The following is a detailed description of embodiments of the present invention with reference to the drawings.

In the Figures:

FIG. 4 is an enlarged plan view in the direction of the arrow IV in FIG. 1,

FIG. 5 is a view similar to FIG. 1 with the hose being shown,

FIG. 6 is a longitudinal section through the open jaws with the hose arranged therebetween and the catheter illustrated below, FIG. 7 is a sectional view along line VII—VII in FIG. 5, FIG. 8 is a sectional view along line VIII—VIII in FIG. 5.

DETAILED DESCRIPTION OF THE PREFERRED EMBODIMENTS

Figure 3:
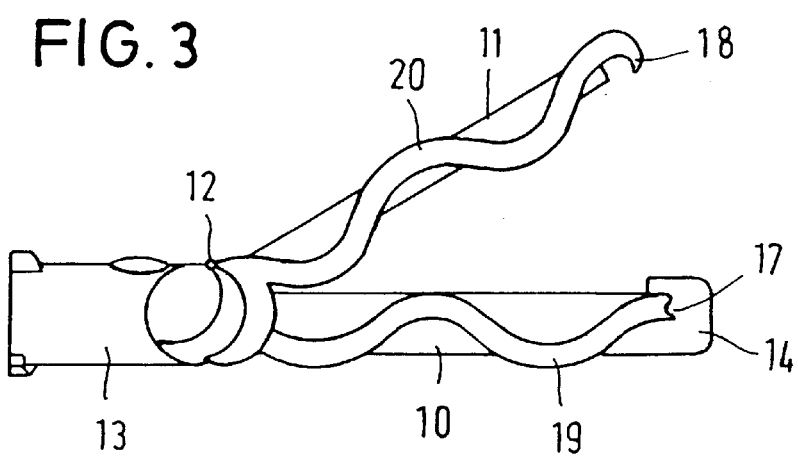
FIG. 3 illustrates the catheter coupling with the jaws open.
Figure 9:
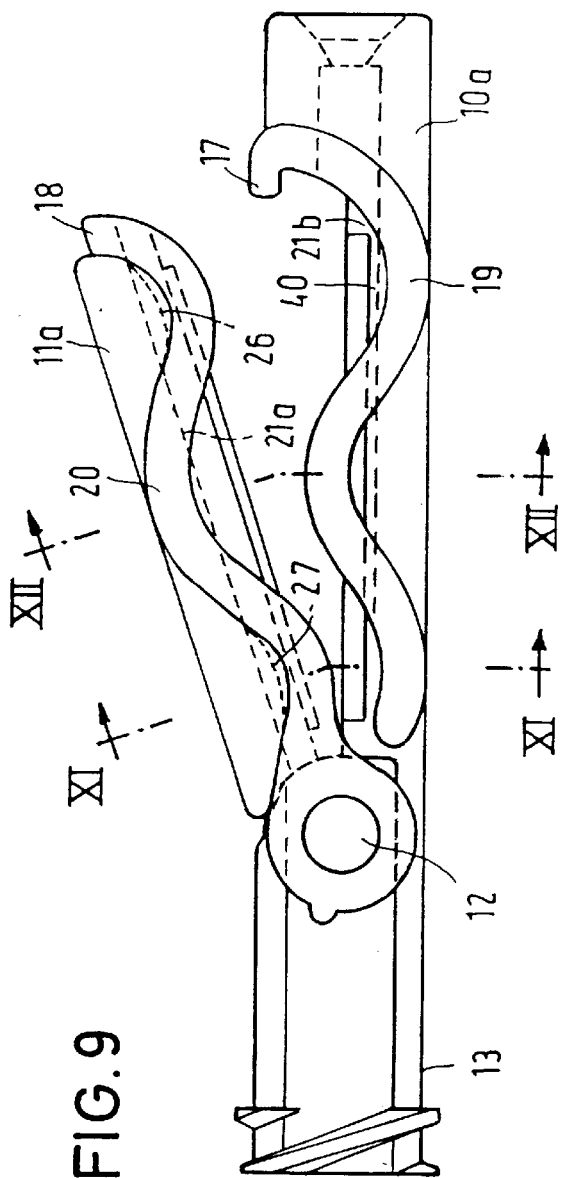
FIG. 9 illustrates another embodiment.

The catheter coupling illustrated comprises two elongate substantially plate-shaped jaws 10, 11 connected at one end by a joint 12. The jaw 10 forms a base jaw rigidly connected with the connecting member 13 and projecting the same axially, whereas the jaw 11 can be folded open, as illustrated in FIG. 3.

At the end averted from the joint 12, the jaw 10 has an end wall 14 with a throughgoing opening 15 for insertion of a catheter. A guiding funnel 16 is formed around the opening 15.

The jaws 10, 11 have interlocking lock elements 17, 18 at the end averted from the joint 12. The lock element 17 consists of a recess at the jaw 10 and the lock element 18 is a resilient hook engaging the recess when the jaw is closed.

Figure 1:
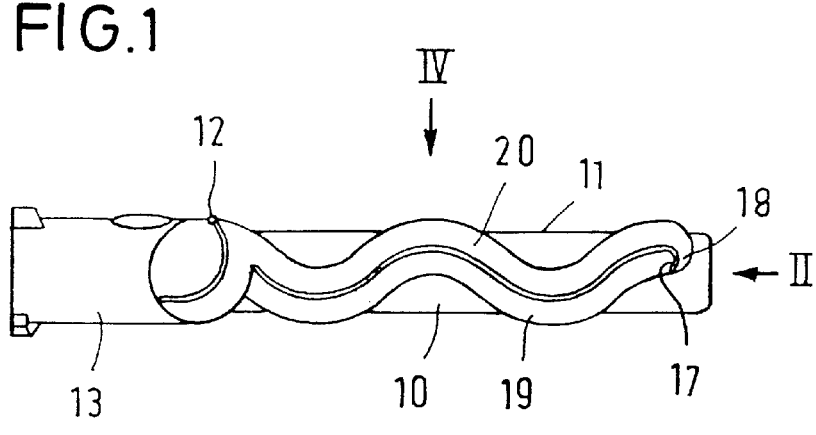
FIG. 1 is a side elevational view of the catheter coupling.
Figure 2:
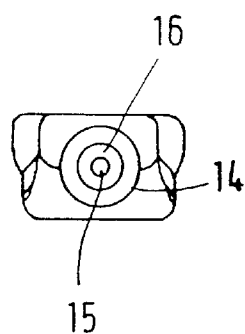
FIG. 2 is a front end view in the direction of the arrow II in FIG. 1.

At its two sides, the jaw 10 has wavy edges 19 and the jaw 11 has matching wavy edges 20. In the closed state of FIG. 1, the edges 19 and 20 abut in a mating manner, whereas the lock elements 17, 18 at the ends of the edges are interlocked.

When closed, the jaws 10, 11 form a longitudinally extending channel 21 that is straight in plan view, as illustrated in FIG. 4, and extends from a passage 22 at the connecting member 13 to the end wall 14. This channel 21, shown dotted in FIGS. 3 and 4, has two bends 23, 23*a*, as illustrated in the side elevational view of FIG. 5. Both bends extend in the same direction, i.e., in the present case, into the jaw 10. Thus, in the bends 23, 23*a*, the channel 21 runs through a depression, respectively. In the section 24 between the bends 23, 23*a*, the channel 21 is straight and extends axial to its end portions. The bends 23, 23*a* and the straight portion 24 each have about the same length. The channel 21 is circular in section. It is formed from a semi-circular groove 21*a* in the upper jaw and a semi-circular groove 21*b* in the lower jaw.

The channel 21 contains a hose piece 25 extending from the passage 22 to the opening 15. The ends of the hose piece 25 may each be glued to the body of the jaw 10. The hose piece 25 is an integral part of the catheter coupling.

When the jaw 11 is opened, the hose piece 25 associated to the jaw 10 takes a straight shape, as illustrated in FIG. 6, lifting itself from the bottom of the two bends 23, 23*a*. The bottom of the groove 21*a* of the upper jaw 11 is provided with two rises 26, 27. The bottom of the groove 21*b* is provided with corresponding recesses 46, 47.

FIG. 6 illustrates the opened state of the jaws. In this state, the proximal end portion of the catheter 30 is inserted into the hose 25 through the opening 15 until the catheter tip 31 is in the passage 22.

The connecting member 13 is made of transparent plastic material. The outer surface of the connecting member is formed with a lens 36 through which the passage 22 can be seen enlarged. Thus, it is easily determined whether the catheter tip 31 is in the appropriate position.

The connecting member 13 is a Luer-Lock plug connector 33 with an inner cone 34 and thread-like projections 35 on its outer surface. The plug connector 33 is plugged with a complementary counter plug connector for connecting the catheter 30 with a liquid source, e.g. via a filter.

It can be seen in FIGS. 7 and 8 that the channel 21 has a constant cross section of the same size in the straight sections 24, as well as in the bends 23, 23*a*. When the jaws 10, 11 are closed, the hose piece 25 is slightly pressed so that it firmly embraces the catheter 30. The strain relief of the catheter is obtained by pressing the hose piece and the catheter therein into the bends 23, 23*a* of the channel 21.

While, in the embodiment illustrated, the bends extend perpendicular at two locations in the groove bottom, escape openings 41, 42 are provided into which the soft material of the hose piece 25 may escape when the upper clamping jaw is closed.

In the embodiment of FIGS. 9–12, the lower and the upper jaws 10*a*, 11*a* are also connected by a joint 12. The opposite ends of the jaws 10*a*, 11*a* are provided with lock elements 17, 18 locking the two jaws relative to each other when the upper jaw 11*a* is closed. For clarity of illustration, the hose piece 25 is not illustrated for the second embodiment. The groove 21 receiving the hose piece 25 has a straight groove bottom 40 without rises or depressions. The groove 21*b* is generally semi-circular in cross section. At two locations in the groove bottom, escape openings 41, 42 are provided into which the soft material of the hose piece 25 may escape when the upper clamping jaw is closed.

As in the first embodiment, the groove bottom of the upper jaw 11*a* is provided with raised portions 26 and 27 separated by a straight section. These raised portions each cause a local squeezing on the straight groove bottom 40 of the lower jaw 10*a* and of the catheter within the hose piece. The raised portions 26, 27 thus compress the hose piece 25.

Figure 12:
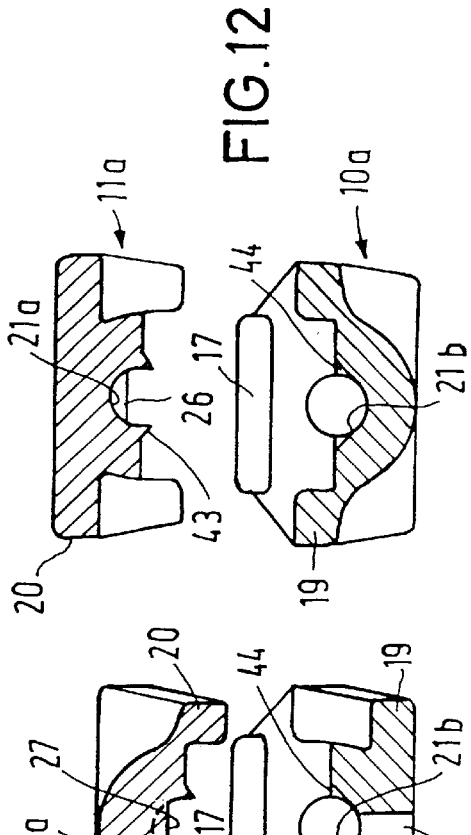
FIG. 12 is a sectional view along line XII—XII of FIG. 9.
Figure 11:
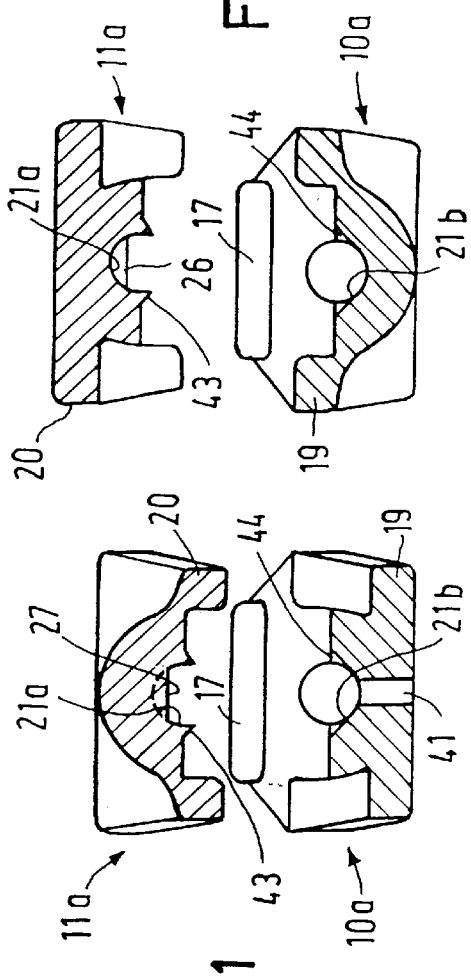
FIG. 11 is a sectional view along line XI—XI of FIG. 9.
Figure 10:
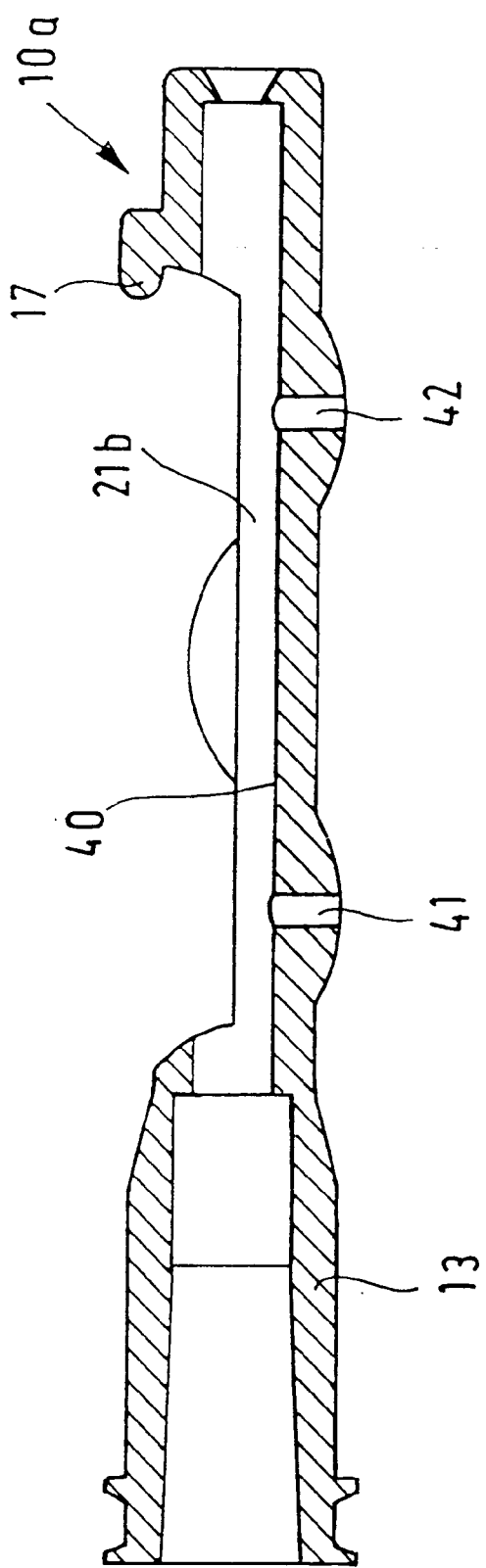
FIG. 10 is a longitudinal section through the lower jaw of the catheter coupling of FIG. 9.

The channel 21 is defined circumferentially by the two opposed grooves 21*a* and 21*b*. As illustrated in FIGS. 11 and 12, one groove 21*a* is provided with longitudinal projections in the form of triangular bars. The opposite groove 21*b* has corresponding recesses 44 into which the projections 43 enter when the jaws are closed. Although the parting plane of the jaws 10*a*, 11*a* extends diametrically through the channel 21, the upper jaw 10*a* embraces more than half of the channel circumference with its longitudinal projections 43, while the lower jaw 11*a* defines less than half the channel circumference because of the recesses 44. The projections 43 prevent the material of the hose piece (not illustrated) within the channel 21 from creeping into the gap between the two jaws. Further, when closing the jaws, a precise guiding is guaranteed.

In the second embodiment, raised portions 26, 27 are provided only at the upper jaw 11*a* so that the cross section of the channel 21 is reduced at the locations of the raised portions 26, 27. At these locations, the hose piece is squeezed.

What is claimed is:

1. A catheter coupling comprising two jaws that, when closed, form a channel; a hose piece for receiving an end portion of a catheter being located in the channel; the jaws being connected at one end by a joint in the longitudinal direction of the hose piece; the jaws having interlocking lock elements at opposite ends; one of the jaws having a groove with at least two successive raised portions; and the opposite jaw having a straight groove.

2. The catheter coupling as defined in claim 1 wherein the jaws are formed such that the channel has at least one constriction of the cross section when the catheter coupling is closed.

3. The catheter coupling as defined in claim 1 wherein the channel has at least two constrictions of the cross section between which extends a longitudinal straight section.

4. The catheter coupling as defined in claim 2 wherein the hose piece is adapted and configured to conform with the at least one constriction of the channel.

5. The catheter coupling as defined in claim 3 wherein the hose piece is adapted and configured to conform with the at least two constrictions of the channel.

6. The catheter coupling as defined in claim 1 wherein the hose piece has dimensions substantially equal to the channel.

7. The catheter coupling as defined in claim 1 wherein one end of the hose piece is in a substantially adjacent communicating relationship with the one end of the jaws and an opposite end of the hose piece is in a substantially adjacent communicating relationship with the opposite ends of the jaws.

8. The catheter coupling as defined in claim 1 wherein the grooves are substantially semi-circular form the channel when the jaws are closed together.

9. The catheter coupling as defined in claim 1 wherein the channel has a cross-section of substantially constant size.

10. The catheter coupling as defined in claim 1 further comprising at least two escape openings in the opposite jaw.

11. A catheter coupling comprising two jaws that, when closed, form a channel; a hose piece for receiving an end portion of a catheter being located in the channel; the jaws being connected at one end by a joint in the longitudinal direction of the hose piece; the jaws having interlocking lock elements at opposite ends; one of the jaws having a plug connector for coupling a counter plug connector thereto; and the one jaw defining one portion of the channel as a whole.

12. The catheter coupling as defined in claim 11, wherein a lens is provided adjacent the plug connector for observing a passage extending between the channel and the plug connector.

13. The catheter coupling as defined in claim 11 wherein the one jaw further defines another portion of the channel as a whole.

14. The catheter coupling as defined in claim 13 wherein the one and the another portions of the channel are located at opposite longitudinal ends of the channel.

15. The catheter coupling as defined in claim 13 wherein one of the opposing ends of the hose piece is affixed in the one portion of the channel and the other end of the hose piece is affixed in the another portion of the channel.

16. The catheter coupling as defined in claim 11 wherein the jaws are formed such that the channel has at least one constriction of the cross section when the catheter coupling is closed.

17. The catheter coupling as defined in claim 11 wherein the channel has at least two constrictions of the cross section between which extends a longitudinal straight section.

18. A catheter coupling comprising two jaws that, when closed, form a channel; a hose piece for receiving an end portion of a catheter being located in the channel; the jaws being connected at one end by a joint in the longitudinal direction of the hose piece; the jaws having interlocking lock elements at opposite ends; and the channel consisting of two grooves one of which being defined by longitudinally extending projections for engaging into corresponding recesses in the other groove.

19. The catheter coupling as defined in claim 18 wherein the jaws are formed such that the channel has at least one constriction of the cross section when the catheter coupling is closed.

20. The catheter coupling as defined in claim 18 wherein the channel has at least two constrictions of the cross section between which extends a longitudinal straight section.

* * * * *